United States Patent
Groux et al.

(10) Patent No.: US 8,076,133 B2
(45) Date of Patent: Dec. 13, 2011

(54) METHOD FOR OBTAINING ANTIGEN-SPECIFIC TR1 REGULATORY LYMPHOCYTES

(75) Inventors: Hervé Groux, Biot (FR); Françoise Cottrez, Biot (FR); Abdelilah Wakkach, Nice (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1419 days.

(21) Appl. No.: 10/477,671

(22) PCT Filed: May 10, 2002

(86) PCT No.: PCT/FR02/01586
§ 371 (c)(1),
(2), (4) Date: Jun. 1, 2004

(87) PCT Pub. No.: WO02/092793
PCT Pub. Date: Nov. 21, 2002

(65) Prior Publication Data
US 2004/0191235 A1    Sep. 30, 2004

(30) Foreign Application Priority Data

May 11, 2001 (FR) ...................... 01 06231

(51) Int. Cl.
*C12N 5/071* (2010.01)
*C12N 5/00* (2006.01)
*C12N 5/02* (2006.01)

(52) U.S. Cl. ...................... 435/372.3; 435/373; 435/377

(58) Field of Classification Search .......... None
See application file for complete search history.

(56) References Cited

U.S. PATENT DOCUMENTS 6,355,479 B1 * 3/2002 Webb et al. .................. 435/325
6,670,146 B2 * 12/2003 Barrat et al. .................. 435/41

FOREIGN PATENT DOCUMENTS

WO    WO 97/29183    8/1997
WO    WO 97/42324    11/1997
WO    WO 9746256 A1 * 12/1997

OTHER PUBLICATIONS

Wakkach et al., Sep. 2001, J. Immunol. vol. 167: 3107-3113.*
Groux et al., 1997, Nature, vol. 389: 737-742.*
Bullens et al., Feb. 2001, Int. Immunol. vol. 13: 181-191.*
Latouche et al., 2000, Nat. Biotech. vol. 18: 405-409.*
Jonuleit, H. et al., Induction of Interleukin 10-producing, Nonproliferating CD4+T Cells with Regulatory Properties by Repetitive Stimulation with Allogeneic Immature Human Dendritic Cells, Nov. 6, 2000; pp. 1213-1222, J. Exp. Med., vol. 192, No. 9.
J. Vingerhoets, et al. "Superantigen Activation of CD4+ and CD8+T Cells From HIV-infected Subjects: Role of Costimulatory Molecules and Antigen-Presenting Cells (APC)." *Clinical and Experimental Immunology*. vol. 111, No. 1, 1998, pp. 12-19. XP002194073.
Hervé Groux, et al. "A CD4+ T-cell Subset Inhibits Antigen-Specific T-cell Responses and Prevents Colitis." *Nature*, MacMillian Journals Ltd., London, vol. 389, No. 6652, 1997, pp. 737-742. XP002164695.

* cited by examiner

*Primary Examiner* — Amy Juedes
(74) *Attorney, Agent, or Firm* — Young & Thompson

(57) ABSTRACT

The invention relates to a method for preparing antigen-specific Tr1 regulatory lymphocytes. The inventive method involves the use of artificial antigen-presenting cells expressing a molecule from the HLA class II system and a human LFA-3 molecule and expressing none of the B7-1, B7-2, B7-H1, CD40, CD23, or ICAM-1 costimulatory molecules.

8 Claims, 1 Drawing Sheet

METHOD FOR OBTAINING ANTIGEN-SPECIFIC TR1 REGULATORY LYMPHOCYTES

Figure 1:
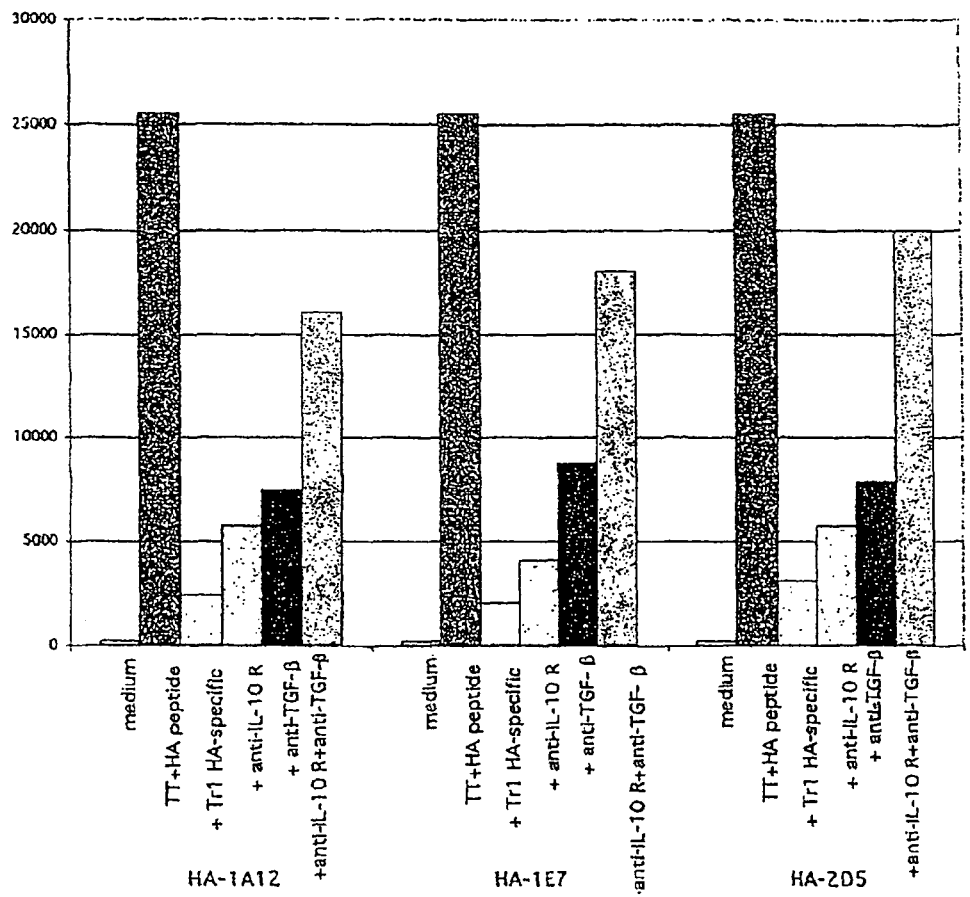

The invention relates to obtaining regulatory $CD4^+$ T lymphocytes which can be used for the prevention and the treatment of autoimmune diseases and inflammatory diseases.

Autoimmune diseases are the result of a deregulation of the immune system, which manifests itself by an undesirable immune response of an organism to its own antigens.

It has been attempted to manipulate the antigens which bring about these pathologies or the aggressive T-cells which are specific for these antigens, but the results obtained have frequently been very limited owing in particular to a lack of knowledge of all the antigens implicated in the pathology in question. This is because the actual auto-antigens, or the antigens which are responsible for inflammatory diseases and autoimmune diseases, are not always known or differ between individuals. The treatments which are currently used against these diseases are either palliative treatments (insulin in the case of diabetes, antihistamine in the case of allergic disorders) or systemic treatments with anti-inflammatories (AINS) and/or immunosuppressants (glucocorticoids, cyclosporin, antibodies and the like). There is therefore clearly a need for an immunosuppressant treatment which is potent, but limited to the affected organ or more precisely to the hyperactivity zone of the immune system.

Among the large number of agents implicated in the regulation of immune response, there are the $CD4^+$ T lymphocytes, also referred to as T-helper lymphocytes. Traditionally, two main types of T-helper lymphocytes are distinguished: the Th1 lymphocytes, which are implicated in the development of the cellular immune response, produce pro-inflammatory cytokines such as interleukin-2 (IL-2) and γ interferon (IFNγ) and have macrophage-activating activity; the Th2 lymphocytes, which produce cytokines such as the interleukins IL-4, IL-6, IL-10 and IL-13, promote the secretion of antibodies.

Recent research, in which one of the inventors has participated, has managed to discover a novel category of regulatory T cells whose proliferation is induced by the activation of $CD4^+$ T cells in the presence of interleukin 10 (IL-10) and which have been called Tr1 lymphocytes (PCT application WO 97/42324). By continuing this research, it has been possible to isolate and characterize a novel subpopulation of regulatory T cells, which were called Tr1 lymphocytes (Groux et al., Nature, 389, 737-742, 1997). This lymphocyte subpopulation has been obtained by repeatedly activating $CD4^+$ T cells in the presence of an antigen and of interleukin 10 (IL-10). When the Tr1 cells are restimulated by the antigen used for their induction, they only proliferate weakly, produce very high amounts of IL-10, high amounts of TGF-β (tumor growth factor β), very small amounts of IL-2 and no IL-4. When activated Tr1 cells are grown in the presence of other $CD4^+$ T cells, they suppress the proliferation of the latter in response to an antigen; this effect is due to the secretion of cytokines, in particular IL-10, by the Tr lymphocytes and not due to a direct action of the latter on the $CD4^+$ T cells; it can therefore be obtained without having to know the antigen which is responsible for the proliferation of these cells. This is of great advantage in the case of autoimmune diseases, where the treatment can thus be envisaged without it being necessary to know the exact antigen against which the pathogenic cells are directed.

It has thus been observed in an experimental model of Crohn's disease in the mouse, in which the proinflammatory cells are directed against commensal bacteria of the gut flora, that the administration to the animals of Tr1 cells which are directed against ovalbumin in conjunction with the administration of ovalbumin in the food allows the institution of chronic inflammation of the colon to be prevented.

Secondly, the inventors have demonstrated in recent research on different animal models of Crohn's disease, of multiple sclerosis or of graft-versus-host reactions, that the inhibitory Tr1 cells were not only capable of preventing, but also of curing, these different pathologies. Moreover, they have observed that the Tr1 cells migrated specifically and intensively into the different sites of inflammation. This characteristic of the Tr1 cells represents an additional advantage in the use of these cells as vectors for anti-inflammatory molecules in the sites of severe inflammation. Tr1 cells obtained from T cells of a patient are therefore potentially useful in the context of a cell therapy for regulating the immune response in this patient. They can thus be used in particular for preventing or treating not only the abovementioned autoimmune diseases and inflammatory diseases, but likewise any other pathology which is characterized by an aberrant inflammatory response such as diabetes, psoriasis, atherosclerosis, rheumatoid polyarthritis or asthma; they can likewise be used in the treatment of graft rejections or of a graft-versus-host reaction.

The method for obtaining Tr1 lymphocytes which is described in the publication of Groux et al. and which is cited hereinabove requires the repeated stimulation of T cells with the antigen in the presence of IL-10. This method is laborious and does not allow to obtain rapidly from a patient a Tr1 lymphocyte population which can be used for a therapeutic treatment.

Different teams have reported the implication of different costimulation molecules in obtaining cells which have characteristics resembling those of Tr1 cells, in particular in the production of IL-10; these stimulation molecules which may be implicated are very diverse and the effects reported sometimes appear to be contradictory.

Thus, Bleijs et al. (Eur. J. Immunol., 29, 2248, 1999) have observed that costimulation by the interaction of LFA-1 with ICAM-1, ICAM-2 or ICAM-3 induces a high production of GM-CSF (granulocyte-macrophage colony-stimulating factor), of IFN-γ and of IL-10 by T lymphocytes which are stimulated with an anti-CD3 antibody. The production of IL-10 is particularly high when the costimulation is carried out by LFA-1/ICAM-1 interaction. Bullens et al. (Int. Immunol. 13, 181-191, 2001) report that costimulation by CD58 induces the production of IL-10 and IFN-γ by T cells which are stimulated by an anti-CD3 antibody. Dong et al. (Nat. Med., 5, 1365, 1999) have described a costimulation molecule which belongs to the B-7 family and is referred to as B7-H1, which induces preferentially the secretion of IL-10.

Van Gool et al. (Eur. J. Immunol., 29, 2367, 1999) have observed that the activation of T cells by an alloantigen in the presence of antibodies which block the CD80/CD28 or CD86/CD28 and CD40/CD40L interactions induced an antigen specific energy which is accompanied by a reduced production of IFN-γ and an increased production of IL-10.

Chabot et al. (J. Immunol., 162, 6819, 1999) report that the production of IL-10 which is induced by the interaction of microglial cells with T lymphocytes is reduced by a blockage of CD40/CD40L, B7/CTLA-4 or B7/CD28, or of CD23.

The inventors have now developed a novel process which allows to obtain antigen-specific Tr1 lymphocytes, rapidly in an amount which is well above the amount obtained by the activation of $CD4^+$ T cells in the presence of IL-10. This is because they have found that growing $CD4^+$ T cells in the presence of an inductor antigen, and cells which present the antigen expressing a class II HLA molecule and the human LFA-3 (CD58) molecule, but which do not express any of the costimulatory molecules B7-1 (CD80), B7-2 (CD86), B7-H1, CD40, CD23 and ICAM-1 (CD54), induced the differentiation of Tr1 cells which are specific for said antigen.

The LFA-3 molecule is the ligand of the CD2 receptor of T lymphocytes. Two forms of LFA-3 have been described: a transmembrane form (Walner et al., J. Exp. Med. 166, 923-932, 1987; PCT Application WO 88/09826), and a form referred to as "PI-linked LFA3", which is anchored to the cell membrane by means of a glycolipid containing phosphatidylinositol (PCT Application WO 90/02181).

The present invention relates to the use of artificial antigen-presenting cells which express a class II molecule of the HLA system and a human LFA-3 molecule and which do not express any of the costimulatory molecules B7-1, B7-2, B7-H1, CD40, CD23 or ICAM-1 (CD54), for obtaining antigen-specific regulatory Tr1 lymphocytes.

Cells which are defined as antigen-specific regulatory Tr1 lymphocytes are cells which have the following characteristics after restimulation with said antigen:
they produce a large amount of IL-10, viz. an amount of $3 \times 10^3$ pg/$10^6$ cells or above, in general $5 \times 10^3$ to $20 \times 10^3$ pg of IL-10 per $10^6$ cells;
they produce an amount of IL-2 of 50 pg/$10^6$ cells or less; the IL-10/IL-2 ratio produced by said cells being at least 50/1, generally 100/1 to 500/1;
they produce an amount of IL-4 of 50 pg/$10^6$ cells or less; the IL-10/IL-4 ratio produced by said cells being at least 300/1, generally 500/1 to 10000/1;
the proliferation of CD4$^+$ T cells stimulated by an antigen in the presence of Tr1 cells is reduced at least 2-fold, in general at least 2 to 100-fold.

In particular, the present invention relates to a method for the preparation of antigen-specific regulatory Tr1 lymphocytes from the lymphocytes of a patient, characterized in that it comprises:
the in vitro activation of said lymphocytes in the presence of the selected antigen, which is presented by artificial antigen-presenting cells as defined hereinabove, and
recovering from said lymphocytes a population of activated CD4$^+$ T lymphocytes comprising at least 10%, preferably at least 50%, very especially preferably at least 80% of Tr1 lymphocytes which are specific for said antigen.

Artificial antigen-presenting cells which can be used for carrying out the present invention can advantageously be obtained by cotransfecting animal cells which do not express any of the above-stated costimulation molecules with a nucleic acid sequence encoding the α chain of a class II HLA molecule, a nucleic acid sequence encoding the β chain of a class II HLA molecule and a nucleic acid sequence encoding any of the two forms of LFA-3. If desired, these cells can likewise be transfected with a nucleic acid sequence encoding the antigen against which the specificity of the Tr1 lymphocytes is to be induced. These nucleic acid sequences can be borne by different nucleic acid molecules or else two or more of them can be borne by the same nucleic acid molecule.

Animal cells which can be used for obtaining said artificial antigen-presenting cells can be cells of human, autologous or heterologous origin or else cells of xenogeneic origin, in particular mammalian cells. Recently isolated primary cultures can be used; in general, it will be preferred to use established cell lines, which are more homogeneous, and capable of proliferating over several generations.

They can take the form of, for example, fibroblasts, keratinocytes, kidney tubule cells, Schwann cells, myoblasts, endothelial cells and the like.

The class II CMH molecule which is expressed by the artificial antigen-presenting cells will be selected from among the different human HLA-2 molecules which are available, depending on the HLA class II type of the patient from which CD4$^+$ T lymphocytes are taken and on the intended use of the Tr1 cells.

In general, artificial antigen-presenting cells will be used which express an HLA-2 molecule which is also expressed by the patient; however, it is also possible to chose an HLA-2 molecule which differs from those expressed by said patient; for example, if it is desired to produce Tr1 cells which can be used for preventing graft rejection, this may take the form of an HLA-2 molecule expressed by the graft cells; in this case, the HLA-2 molecule constitutes the antigen against which the Tr1 cells obtained will be directed. The antigen used for carrying out the method according to the invention will be chosen depending on the use for which the antigen-specific Tr1 cells to be produced are intended. The antigen can take the form of an antigen associated with an inflammatory or autoimmune pathology; likewise, it may take the form of an antigen without relation to a particular pathology but which can be administered if the Tr1 cells are to be activated to control an undesirable immune response.

The artificial antigen-presenting cells can be charged with the antigen in the traditional manner by coincubating the cells and said antigen. The latter can be present in native form and be prepared by said antigen-presenting cells; it can likewise be present in the form of one or more antigenic peptides which can be attached directly by the HLA-2 molecules which are expressed by said cells. Alternatively, the antigen can be expressed by the artificial antigen-presenting cells when the latter have previously been transfected with a nucleic acid sequence encoding it.

For carrying out the method according to the invention, the in vitro activation of the lymphocytes can be carried out directly on PBMCs (peripheral blood mononuclear cells) taken from said patient. It can also be carried out on CD4$^+$ T lymphocytes which have previously been isolated from these PBMCs.

The lymphocytes are activated by coculturing them over 2 to 10 days, preferably over 6 to 8 days, in the presence of the above-described artificial antigen-presenting cells which are charged with the selected antigen.

At the end of this culture period, the activated CD4$^+$ T lymphocytes are selected on the basis of the expression of the CD4$^+$ marker and one or more activation markers such as CD25, CD69, CD45RO and the like.

At the end of this culture period, a cell population is obtained in which the Tr1 lymphocytes account for at least 10%, in general for between 50 and 80%, of the activated antigen-specific T lymphocytes.

To concentrate the Tr1 lymphocytes even more in this population, the stimulation under the above-defined conditions may be repeated.

Thus, a population of activated CD4$^+$ T lymphocytes is obtained which comprises at least 30%, in general between 60 and 90%, of Tr1 lymphocytes among the antigen-specific T cells.

Likewise, Tr1 lymphocyte clones can be isolated from this population. These clones can be identified readily on the basis of the characteristic cytokine production profile of the Tr1 lymphocytes as defined hereinabove.

Clone propagation may be carried out in a nutrient medium comprising unspecific growth factors such as IL-4 and IL-2. A preferred embodiment consists in using anti-CD3- and anti-CD28-antibody-coupled beads as stimulation agent.

The Tr1 cells obtained by the method according to the invention present all the characteristics of the Tr1 cells obtained by activation of CD4+ T lymphocytes in the presence of IL-10 and have therefore the same applications as the latter for regulating the immune response.

The present invention also relates to a process for the preparation of a pharmaceutical composition intended for the treatment of inflammatory diseases and/or autoimmune diseases, characterized in that it comprises preparing antigen-specific Tr1 lymphocytes by a method according to the invention and packaging said Tr1 lymphocytes in a formulation which is suitable for their administration to a patient.

The present invention will be understood better with the aid of the remainder of the description which follows, which relates to nonlimiting examples which illustrate how the method according to the invention is carried out.

Example 1

Preparation of Tr Lymphocytes

Isolation of CD4+ T Cells
Peripheral mononuclear cells (PBMCs) are obtained by centrifugation on Ficoll-Hypaque.

The CD4+ T cells are obtained by eliminating the non-CD4+ cells using anti-CD8 (L533), anti-CD11b (OKM1), and anti-CD20 (2H7) antibodies as described in the following protocol. The cells are incubated for 20 minutes at 4° C. with saturating antibody concentrations. After washing, Dynabeads (Dynal, Oslo, Norway) are added at a bead/target cell ratio of 1/1, and the mixture is incubated for 1 hour at 4° C. The beads which have the non-CD4+ cells attached to them are eliminated by application of a magnetic field. Analysis of the remaining cells by flow cytofluorometry (FACSstar, Becton Dickinson) demonstrates that they comprise 90 to 95% CD4+ T cells.

Obtaining the Artificial Antigen-Presenting Cells
Murine L fibroblast cells (ATCC CCL-1) were cotransfected with nucleic acid sequences encoding LFA-3 and a class II HLA molecule.

Obtaining a LFA-3-Encoding cDNA
An LFA-3-encoding cDNA was prepared from a complete cDNA library of human peripheral mononuclear cells by means of polymerase chain reaction (PCR) using the primer referred to as 5'LFA-3, which comprises the sequence of nucleotides 13 to 33 of the sequence encoding human LFA-3 (Genbank Access Number X06296), flanked 5' by a KpnI site, and the primer referred to as 3'LFA-3, which comprises the sequence of nucleotides 708 to 728 of the sequence encoding human LFA-3, flanked 5' by an NotI site.

Obtaining a DR1-Encoding cDNA
A cDNA encoding the DR1 alpha chain was obtained from a complete cDNA library of human peripheral mononuclear cells from a DR1+ donor by polymerase chain reaction (PCR) using the primers referred to as DR1A5' and DR1A3', which comprise the sequence of nucleotides 151 to 176 and the sequence of nucleotides 769 to 792, respectively, of the sequence encoding the DR1 alpha chain (Genbank Access Number K01171). A cDNA encoding the DR1 beta chain was obtained in the same manner using the primers referred to above as DR1B5' and DR1B3', which comprise the sequence of nucleotides 52 to 74 and 850 to 923, respectively, of the sequence encoding the DR1 beta chain (Genbank Access Number NM002124).

Transfection of the Cells
Each of the cDNAs obtained was cloned into the TA site of a vector pcDNA 3.1/hygro (Invitrogen). The vectors obtained were used for cotransfecting the L cells by electroporation.

The stable transfectants are separated by flow cytofluorometry (FACSVantage SE, Becton Dickinson) by labeling the cells with the aid of an anti-LFA-3 antibody (1C3) and anti-DR antibody (L243). The cells which express LFA-3 and DR simultaneously are retained and cultured on F12 medium (Life Technologies) supplemented with 10% fetal calf serum (Boehringer) with added penicillin and streptomycin.

Antigen-presenting cells which coexpress LFA-3 and DR1 were likewise prepared as described above by cotransfecting P815 cells (ATCC-TIB64).

Untransfected L cells or P815 cells, or cells obtained by transfection of L cells or P815 cells which express only the DR1 molecule, were likewise used by way of control.

Obtaining the Tr Lymphocytes
CD4+ T cells isolated as described hereinabove from PBMCs of a non-DR1 donor are suspended at a concentration of $2\times10^6$ cells/ml in Yssel medium (Yssel et al., J. Immunol. Methods, 72, 219-227, 1984). The cell suspension is divided in a 24-well culture plate at 1 ml per well. The transfected L-DR1-LFA3 cells or the transfected L-DR1 cells, which have been obtained as described hereinabove, or, by way of control, B-EBV DR1+ lymphoblastoid cells are irradiated (60 GY) and added to each well at a concentration of $5\times10^5$ cells/ml.

After incubation for 7 days, the cells are harvested and washed in PBS and then labeled with the aid of anti-CD4 antibody (RPA-T4) and anti-CD25 antibody (M-A251). The CD4+CD25+ cells are separated by flow cytofluorometry and cloned at 1 cell/well in a 96-well plate in Yssel medium. Clonal propagation is carried out in the presence of IL-2 and IL-4 by the technique described by Spits and Yssel (J. Immunol. Methods, 9, 416-421, 1996). After the propagation of the clones, the different clones are restimulated with B-EBV DR1+ lymphoblastoid cells. 48 hours after the stimulation, the cell supernatant is recovered and the profile of the production of cytokines IL-10 and IFN-γ in response to this stimulation was determined by quantitatively determining these cytokines by ELISA in accordance with the protocol described by Abrams et al. (Curr. Protocols Immunol., 13, pp 6.1-6-15, 1995).

The results illustrated in Table I hereinbelow represent the production of cytokines IL-10 and IFN-γ by Tr1 cells (mean±standard deviation of 10 clones) from 2 different donors

TABLE I

| Cell | Donor 1 | | Donor 2 | |
| --- | --- | --- | --- | --- |
| | IL-10 (pg/ml) | IFN-γ (pg/ml) | IL-10 (pg/ml) | IFN-γ (pg/ml) |
| L-DR1 | 326 ± 40 | 13372 ± 1500 | 3657 ± 324 | 9638 ± 63 |
| L-DR1-LFA-3 | 2315 ± 183 | 19403 ± 975 | 6402 ± 272 | 914 ± 322 |
| B-EBV DR1+ | <40 | 16005 ± 123 | 174 ± 59 | 4930 ± 685 |

In another experimentation series, the CD4+ T cells isolated from PBMCs from a DR1+ donor are mixed as described hereinabove with antigen-presenting cells expressing the DR1 molecule and the LFA-3 molecule.

An inductor antigen (peptide HA 307-319, which corresponds to a fragment of the capsid antigen of the virus *Haemophilus influenzae*) is added to the cell mixture at a concentration of 50 µg/ml.

After incubation for 3 days, the CD4$^+$CD25$^+$ cells are separated by flow cytofluorometry and cloned as described hereinabove.

After the propagation of clones, the different clones are restimulated with B-EBV lymphoblastoid cells charged with the HA peptide (10 μM). 48 hours after the stimulation, the cell supernatant is recovered and the profile of the production of the cytokines IL-2, IL-4, IL-10 and IFY-γ in response to this stimulation was determined by quantitative determination of these cytokines by means of ELISA in accordance with the protocol described by Abrams and co-workers.

Most (approximately 70%) of the CD4$^+$CD25$^+$ clones isolated present the cytokine production profile of TR1 cells.

The cytokine production profiles of 9 of these Tr1 clones are illustrated by Table II hereinbelow.

TABLE II

| Clone | IL-2 (pg/ml) | IL-4 (pg/ml) | IL-10 (pg/ml) | IFN-γ (pg/ml) |
|---|---|---|---|---|
| HA-1A12 | <20 | <40 | 12358 | 521 |
| HA-IB6 | <20 | <40 | 11897 | 497 |
| HA-IC9 | <20 | <40 | 14598 | 1369 |
| HA-IE5 | <20 | <40 | 13549 | 314 |
| HA-IE7 | 40 | <40 | 11697 | 876 |
| HA-IF2 | <20 | <40 | 10597 | 1057 |
| HA-2B6 | <20 | <40 | 17891 | 697 |
| HA-2D5 | 32 | <40 | 16589 | 503 |
| HA-2F2 | <20 | <40 | 17803 | 873 |

Tr1 cell clones with the same cytokine production profile have also been obtained using P815-DR1-LFA-3 cells as antigen-presenting cells, which demonstrates that obtaining Tr1 cells is not linked to the characteristics of the cell line from which the antigen-presenting cells are obtained.

Example 2

Immunoregulatory Characteristics of TR1 Lymphocytes Obtained by the Method According to the Invention The immunoregulatory characteristics of antigen-specific Tr1 cells were tested as follows:

Human CD4$^+$ T cells from a DR1$^+$ donor (1×10$^6$/ml) are stimulated by irradiated (60 GY) syngenic monocytes (1×10$^6$/ml) in the presence of the peptide HA 307-319 (50 μM) and of tetanus anatoxin (TT: 50 μg/ml).

The same experiment is carried out in parallel, adding an HA-specific Tr1 clone obtained as described above to the cells (2×10$^5$/ml), alone or in the presence of an antibody directed against the IL-10 receptor (anti-IL-10R, 10 μg/ml), of an anti-TGF-β antibody (20 μg/ml) or of a mixture of these 2 antibodies.

The proliferation of the CD4$^+$ T cells is determined after 5 days by measuring the incorporation of tritiated thymidine.

The results obtained for 3 HA-specific Tr1 clones are, illustrated in FIG. 1.

Key to FIG. 1:

X-axis: proliferation (incorporated tritiated thymidine, in cpm).

Y-axis:

Medium: non-stimulated CD4$^+$ T cells;

TT$^+$ HA peptide: CD4$^+$ T cells stimulated by the peptide HA 307-319 and the tetanus anatoxin;

$^+$Tr1 HA specific: CD4$^+$ T cells stimulated by the peptide HA 307-319 and the tetanus anatoxin in the presence of Tr1 cells which are specific for the HA antigen;

$^+$anti IL-10R: CD4$^+$ T cells stimulated by the peptide HA 307-319 and the tetanus anatoxin in the presence of Tr1 cells which are specific for the HA antigen and of anti-IL-10R antibodies;

$^+$anti-TGF-β: CD4$^+$ T cells stimulated by the peptide HA 307-319 and the tetanus anatoxin in the presence of Tr1 cells which are specific for the HA antigen and of anti-TGF-β antibodies;

$^+$anti IL-10R$^+$anti-TGF-β: CD4$^+$ T cells stimulated by the peptide HA 307-319 and the tetanus anatoxin in the presence of Tr1 cells which are specific for the HA antigen and of a mixture of anti-IL-10R antibodies and anti-TGF-β antibodies.

These results demonstrate that the Tr1 lymphocytes obtained by the process according to the invention diminish considerably the antigen-specific proliferation of CD4$^+$ T cells. This inhibitory effect is only very weakly attenuated by anti-IR-10R antibodies or anti-TGF-β antibodies alone and is partially annulled by a mixture of the 2 antibodies.

We claim:

1. A method of preparing antigen-specific regulatory Tr1 lymphocytes by activation and differentiation of CD4+ lymphocytes of a subject, comprising:

separating lymphocytes from a sample of the subject's blood, activating said lymphocytes in vitro by co-culturing with artificial antigen-presenting cells comprising cells which express a class II molecule of the HLA system and a human LFA-3 molecule and which do not express any of the costimulatory molecules B7-1, B7-2, B7-H1, CD40, CD23 or ICAM-1, and which present a selected antigen associated to the class II molecule, recovering from said activated lymphocytes a population of activated CD4+ T lymphocytes comprising at least 10% of Tr1 lymphocytes which are specific for the antigen of the antigen-presenting cells, and isolating said Tr1 lymphocytes from said population of activated CD4+ T lymphocytes to produce said antigen-specific regulatory Tr1 lymphocytes.

2. The method of claim 1, wherein the artificial antigen-presenting cells are obtained by co-transfection of mammalian cells selected from the group consisting of fibroblasts, keratinocytes, kidney tubule cells, Schwann cells, myoblasts and endothelial cells, with a nucleic acid sequence encoding the α chain of a class II HLA molecule, a nucleic acid sequence encoding the β chain of a class II HLA molecule and a nucleic acid sequence encoding human LFA-3.

3. The method as claimed in claim 1, wherein the antigen-presenting cells have a selected antigen associated with them and further comprising activating the lymphocytes in vitro with said selected antigen in addition to the antigen-presenting cells in the activating step.

4. The method of claim 1, wherein the antigen-specific regulatory Tr1 lymphocytes produce more IL-10 than IFNγ.

5. A method of preparing antigen-specific regulatory Tr1 lymphocytes by activation and differentiation of CD4+ lymphocytes of a subject, comprising:

separating lymphocytes from a sample of the subject's blood, activating said lymphocytes in vitro by co-culturing with artificial antigen-presenting cells comprising cells which express a class II molecule of the HLA system and a human LFA-3 molecule and which do not express any of the costimulatory molecules B7-1, B7-2, B7-H1, CD40, CD23 or ICAM-1, and which present a selected antigen associated to the class II molecule, recovering from said activated lymphocytes a population of activated CD4+ T lymphocytes comprising at least 10% of Tr1 lymphocytes which are specific for the antigen of the antigen-presenting cells, repeating the activating step by activating the recovered population of CD4+ T lymphocytes in vitro with said antigen-presenting cells, and enriching the population of activated CD4+ lymphocytes to at least 30% Tr1 lymphocytes that are specific for the selected antigen, and isolating said Tr1 lymphocytes from said population of activated CD4+ T lymphocytes to produce said antigen-specific regulatory Tr1 lymphocytes.

6. A method of preparing antigen-specific regulatory Tr1 lymphocytes by activation and differentiation of CD4+ lymphocytes of a subject, comprising:

separating lymphocytes from a sample of a subject's blood, activating said lymphocytes in vitro by co-culturing with artificial antigen-presenting cells comprising cells which express a class II molecule of the HLA system and a human LFA-3 molecule and which do not express any of the costimulatory molecules B7-1, B7-2, B7-H1, CD40, CD23 or ICAM-1, and which present a selected antigen associated to the class II molecule, recovering from said activated lymphocytes a population of activated CD4+ T lymphocytes comprising at least 10% of Tr1 lymphocytes which are specific for the antigen of the antigen-presenting cells, isolating Tr1 lymphocyte clones from said recovered population of activated CD4+ T lymphocytes, and propagating the isolated Tr1 lymphocyte clones.

7. The method of claim 6, wherein the artificial antigen-presenting cells are obtained by co-transfection of mammalian cells selected from the group consisting of fibroblasts, keratinocytes, kidney tubule cells, Schwann cells, myoblasts and endothelial cells, with a nucleic acid sequence encoding the α chain of a class II HLA molecule, a nucleic acid sequence encoding the β chain of a class II HLA molecule and a nucleic acid sequence encoding human LFA-3.

8. The method of claim 6, wherein said lymphocytes are activated in vitro by co-culturing with the selected antigen in addition to the antigen-presenting cells.

* * * * *